(12) United States Patent
Daum et al.

(10) Patent No.: US 6,365,339 B1
(45) Date of Patent: Apr. 2, 2002

(54) GENDER DETERMINATION OF AVIAN EMBRYO

(75) Inventors: Keith A. Daum; David A. Atkinson, both of Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/389,660

(22) Filed: Sep. 2, 1999

Related U.S. Application Data (60) Provisional application No. 60/099,171, filed on Sep. 4, 1998.

(51) Int. Cl.⁷ .................................................. C12Q 1/00
(52) U.S. Cl. ............................ 435/4; 530/827; 530/851
(58) Field of Search ..................... 435/4, 807; 436/906; 530/359, 412, 827, 851

(56) References Cited

U.S. PATENT DOCUMENTS

| | | | |
|---|---|---|---|
| 4,629,689 A | * 12/1986 | Diamond et al. ............... 435/7 |
| 5,377,618 A | 1/1995 | Crews et al. ................ 514/182 |
| 5,508,165 A | 4/1996 | Halverson et al. ............. 435/6 |
| 5,648,468 A | 7/1997 | Spaulding .................... 530/359 |
| 5,679,514 A | 10/1997 | Baker ............................. 435/6 |
| 5,707,809 A | 1/1998 | Halverson et al. ............. 435/6 |

FOREIGN PATENT DOCUMENTS

| WO | WO 99/34667 | * 7/1999 |
|---|---|---|

OTHER PUBLICATIONS

Distler W. Prenatal Sex Determination by Radioimmunoassay of Testosterone. Arch Gynecol 227(1)7–12, Mar. 1989.*
Hill, Herbert H., Jr., et al, "Ion Mobility Spectrometry," *Analytical Chemistry*, vol. 62, No. 23, Dec. 1, 1990 pp. 1201A–1208A.

* cited by examiner

*Primary Examiner*—Ralph Gitomer
(74) *Attorney, Agent, or Firm*—Pedersen Clark PLLC (57) ABSTRACT

Disclosed is a method for gender determination of avian embryos. During the embryo incubation process, the outer hard shells of eggs are drilled and samples of allantoic fluid are removed. The allantoic fluids are directly introduced into an ion mobility spectrometer (IMS) for analysis. The resulting spectra contain the relevant marker peaks in the positive or negative mode which correlate with unique mobilities which are sex-specific. This way, the gender of the embryo can be determined.

7 Claims, 9 Drawing Sheets

GENDER DETERMINATION OF AVIAN EMBRYO

RELATED APPLICATION

This application claims priority from provisional application Ser. No. 60/099,171 filed Sep. 4, 1998; hereby, incorporated by reference.

CONTRACTUAL ORIGIN OF THE INVENTION

The United States Government has rights in this invention pursuant to Contract No. DE-AC07-94ID 13223 between the United States Department of Energy and Lockheed Martin Idaho Technologies Company.

DESCRIPTION

BACKGROUND OF THE INVENTION

1. Field of the Invention

This invention relates generally to gender determination of bird eggs. More specifically, this invention relates to egg gender determination by analysis of sex-specific compounds in allantoic fluid of the egg by ion mobility spectrometry (IMS).

2. Related Art

A common method for sexing birds is the Japanese method of vent sexing which involves manual procedures and requires trained professionals with highly specialized skills. Another common method involves feather sexing of chicks which carry the a slow feathering gene. However, birds which carry this slow feathering gene also exhibit slower growth and reduced egg production. There are other methods, such as illumination of the egg to determine eye color at day 10, polymerase chain reaction (PCR), immunoassay, and DNA based techniques. All of these techniques have problems with speed, cost effectiveness, or negative production effects.

For example, U.S. Pat. No. 5,377,618 (Crews et al.) and U.S. Pat. No. 5,648,468 (Spaulding) disclose methods for urging the sex of avian embryos. Crew et al. uses an injection of estradiol-17 beta for female development and dihydrotestosterone for male development. Spaulding uses isolated sex-specific proteins to create antibodies for immunoassays and for injection back into the hen to create sex selection pressure.

Also, U.S. Pat. No. 5,508,165 (Halverson et al. '165), U.S. Pat. No. 5,679,514 (Baker), and U.S. Pat. No. 5,707,809 (Halverson et al. '809) disclose methods for determining the sex of avian embryo by DNA techniques.

SUMMARY OF THE INVENTION

Ion mobility spectrometry (IMS) offers a technique that can provide reliable results quickly, uses current genetic strains, and is less traumatic to the birds. IMS also may be integrated into current hatchery process equipment (i.e. vaccination equipment) as an automated technique that is labor-saving and cost effective. With the invented technique based on IMS, the sex of resulting birds can be determined prior to hatching from the egg, allowing the poultry industry to realize significant cost and labor savings while processing tens of millions of eggs per day.

According to the invention, during the incubation process, the outer hard shells of eggs are drilled and samples of allantoic fluid are removed. This process does not intrude into the embryo or amniotic fluid. The allantoic fluids are directly introduced into an ion mobility spectrometer (IMS) for analysis, for example, of estradiol or other sex-specific compound. The resulting spectra contain the relevant marker peaks with unique mobilities that are sex-specific. In the negative mode, peaks with reduced mobilities around 2.0 were found in eggs with female embryos and peaks with reduced mobilities from 1.5 to 1.25 were found in eggs with male embryos. In the positive mode, there were peaks at reduced mobilities of about 1.6 found in eggs with male embryos and peaks with reduced mobilities of about 1.4 found in eggs with female embryos. There were also sex-specific peaks at lower intensities at other reduced mobilities. Based on these data, sex determination may be made based on the presence or absence of one or several of these peaks or combinations of these peaks. As may be seen, sex determination may also be accomplished in either the positive or negative mode of IMS.

Allantoic fluids were analyzed directly by direct injection of microliter quantities into the IMS source region. The small quantities needed for analysis translate well into an online process which may be integrated with existing inoculation equipment. Sample preparation in this preferred method is minimal to non-existent, thus enhancing sample throughput. The egg fluid may be able to be analyzed quickly and without sample preparation by direct injection of the fluid into the IMS source region.

DESCRIPTION OF THE PREFERRED EMBODIMENTS

There has been a need to determine chemical markers in egg fluids that indicate the sex of unborn chickens. This is important because eggs containing hens may be separated and further developed for egg production. Also, eggs containing roosters may be separated and further developed for meat production.

From past research, estradiol was identified as a potential chemical marker to identify female eggs from allantoic fluids. However, the estradiol levels were identified as being very low (picograms/milliliter of fluid). Ion mobility spectrometry (IMS) was chosen for this application due to its sensitivity, rapid response time, and flexible sample introduction requirements. IMS has picogram level sensitivity for many compounds, and was therefore considered a potential solution. IMS could also be used to directly analyze the egg fluids; this could be a great advantage in designing a high throughput sexing system.

IMS, a highly sensitive detection and analytical technique, was developed in the 1970's. An update on the technique is published at *Analytical Chemistry*, Vol. 62, No. 23 (December 1990), pp. 1201A–1209A, which report is hereby incorporated by reference.

Allantoic fluids are the preferred source for chemical markers for determining the sex of the chick because these waste-like fluids are more closely related to the chick than to either of its parents. However, other sources of fluids from the egg may also be used.

Other chemical markers besides estradiol may also be analyzed by this method. For example, dihydrotestosterone may be a marker to identify male eggs. Also, other sex-specific markers may be used.

Experimental

As a first step, IMS spectra were taken of neat estradiol crystals and of samples prepared by dissolution of estradiol in both acetone and methanol. Acetone and methanol are common IMS solvents and their background spectra are well known.

The next step was to directly analyze the allantoic fluid samples to determine if differences exist due to sex. Microliter level direct injections of the allantoic fluid into the IMS were used. The sex of the egg embryos were later determined by conventional techniques.

Data

Figure 1:
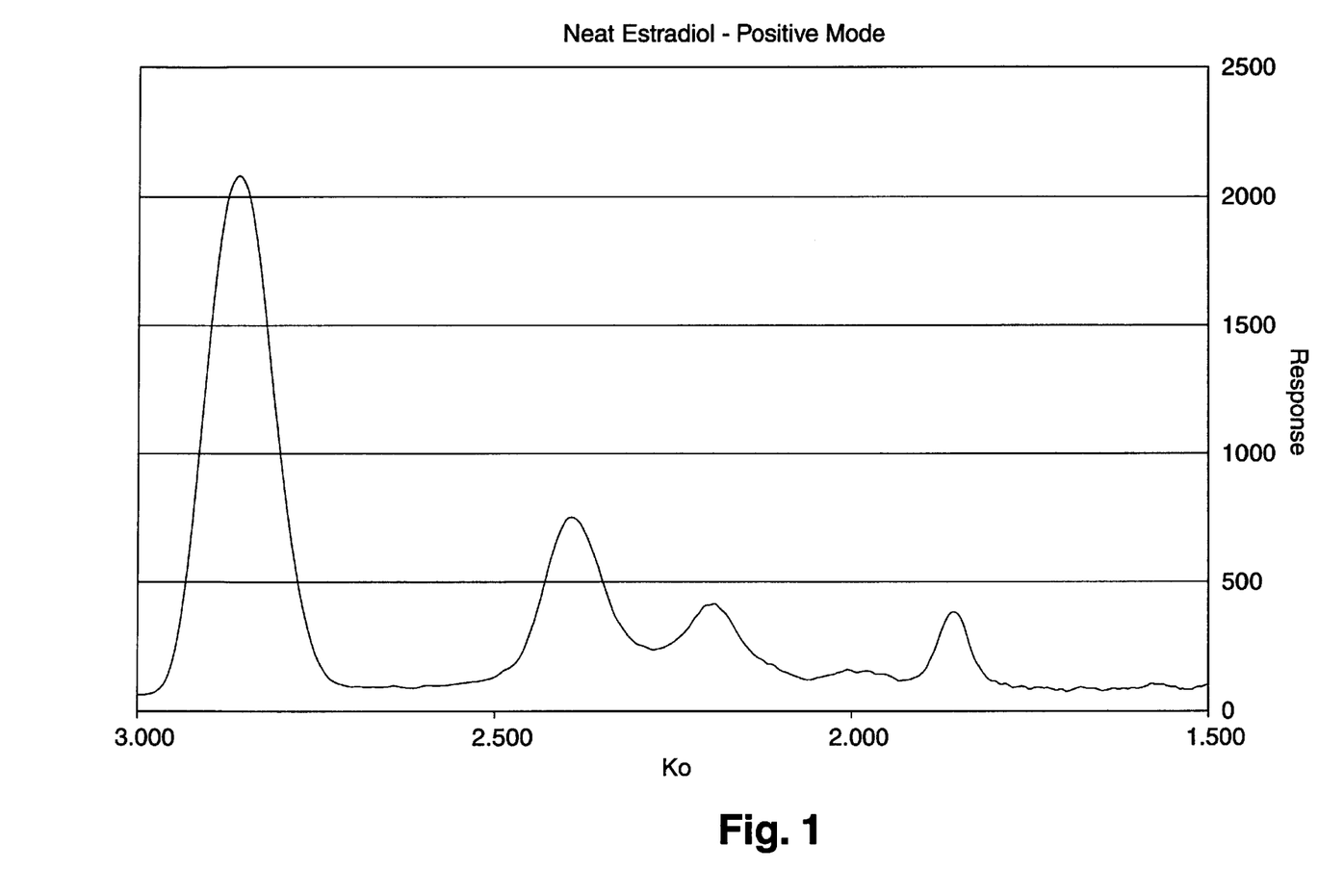
FIG. 1 is a positive mode ion mobility spectrometry (IMS) spectra of neat estradiol crystals.
Figure 2:
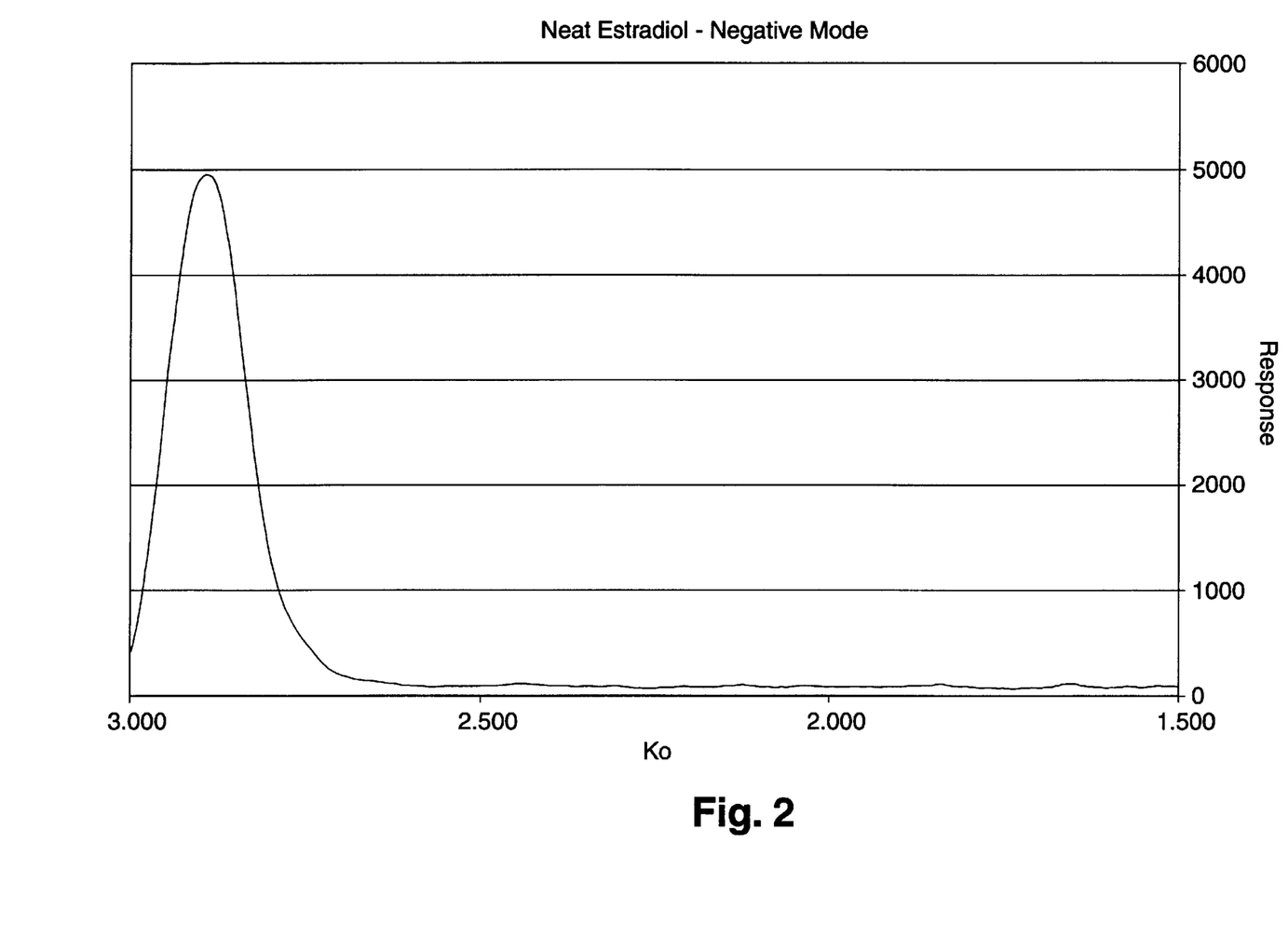
FIG. 2 is a negative mode IMS spectra of neat estradiol crystals.
Figure 3:
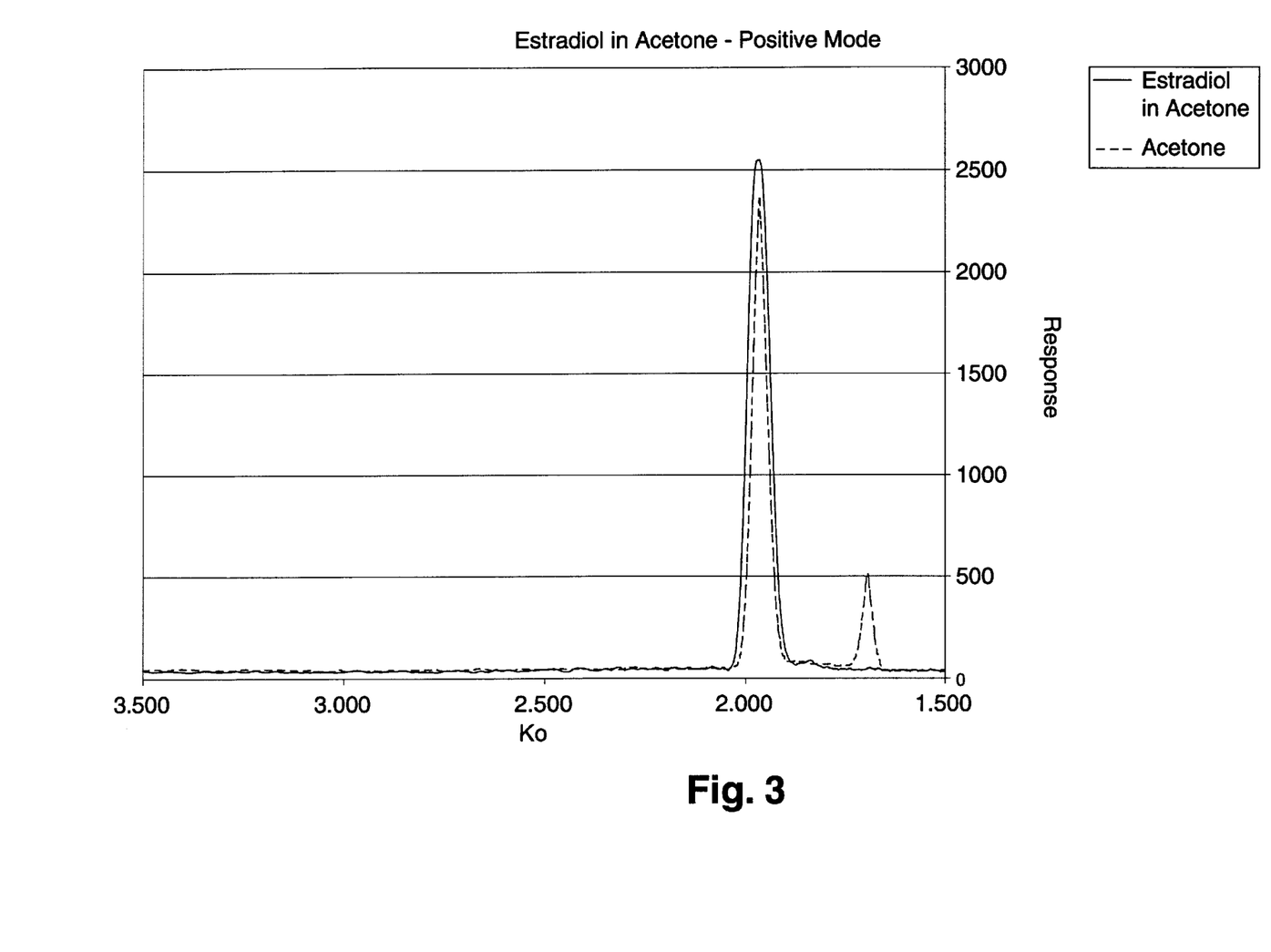
FIG. 3 is a positive mode IMS spectra of estradiol crystals dissolved in acetone.
Figure 4:
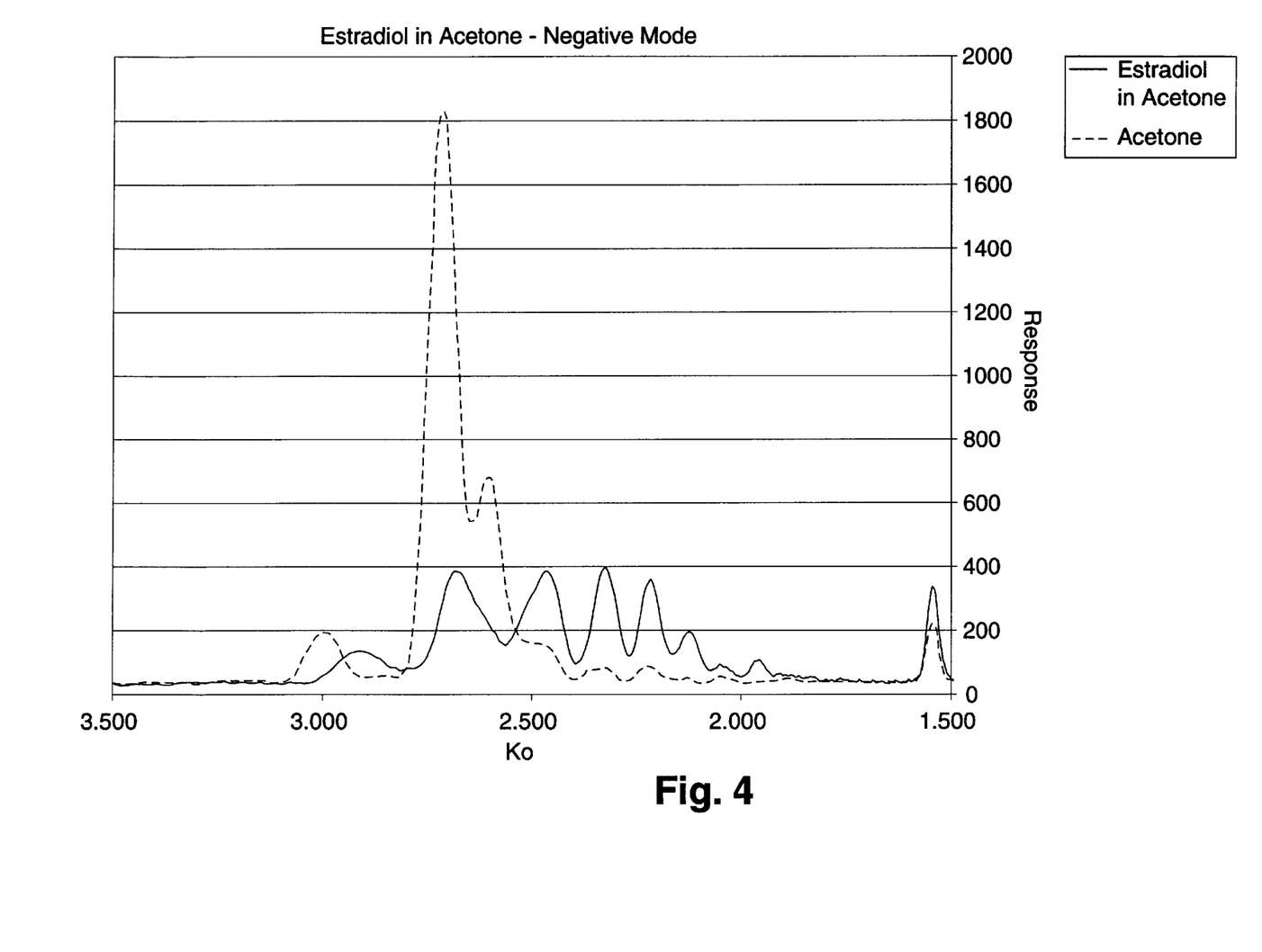
FIG. 4 is a negative mode IMS spectra of estradiol crystals dissolved in acetone.
Figure 5:
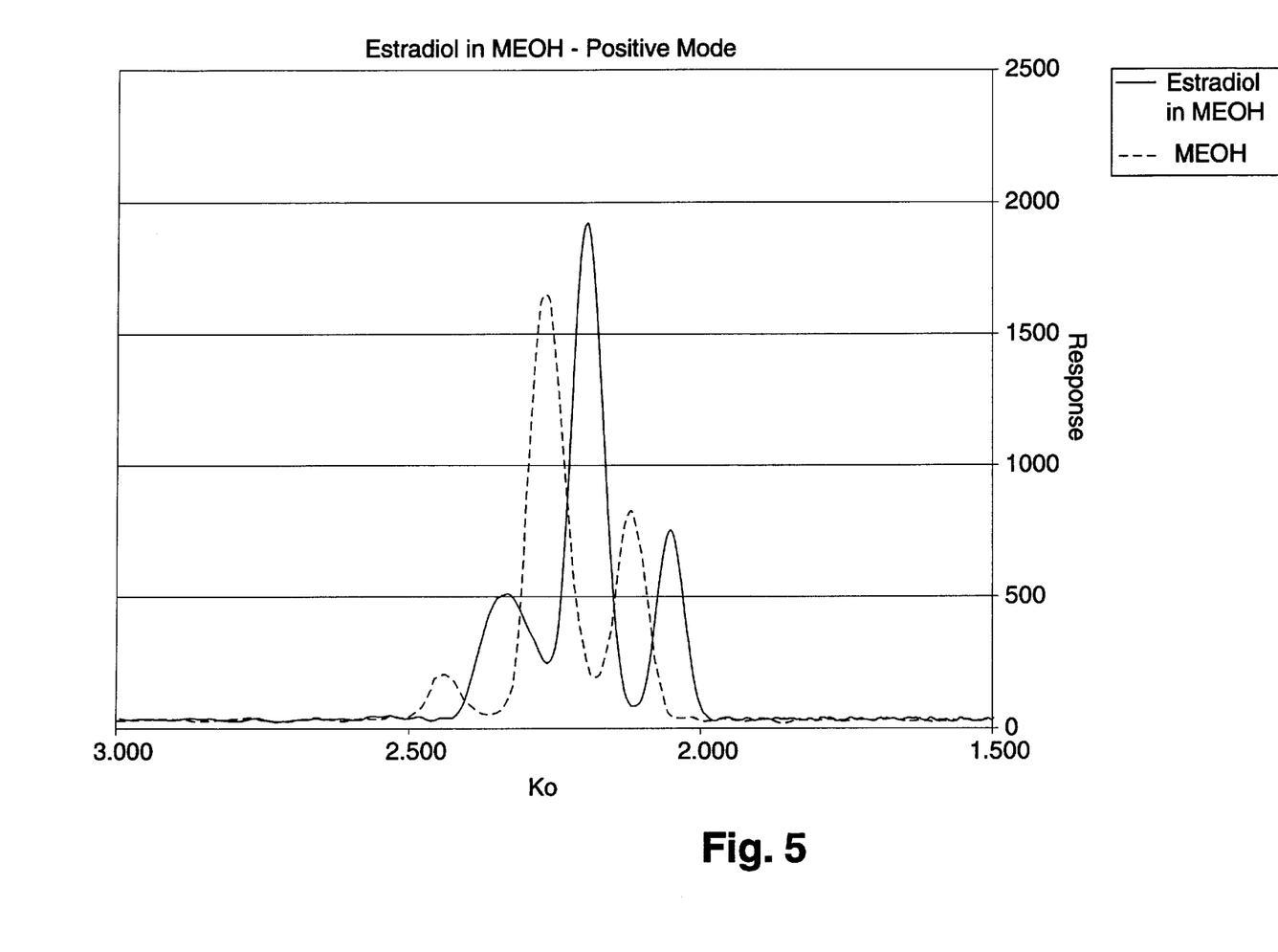
FIG. 5 is a positive mode IMS spectra of estradiol crystals dissolved in methanol.
Figure 6:
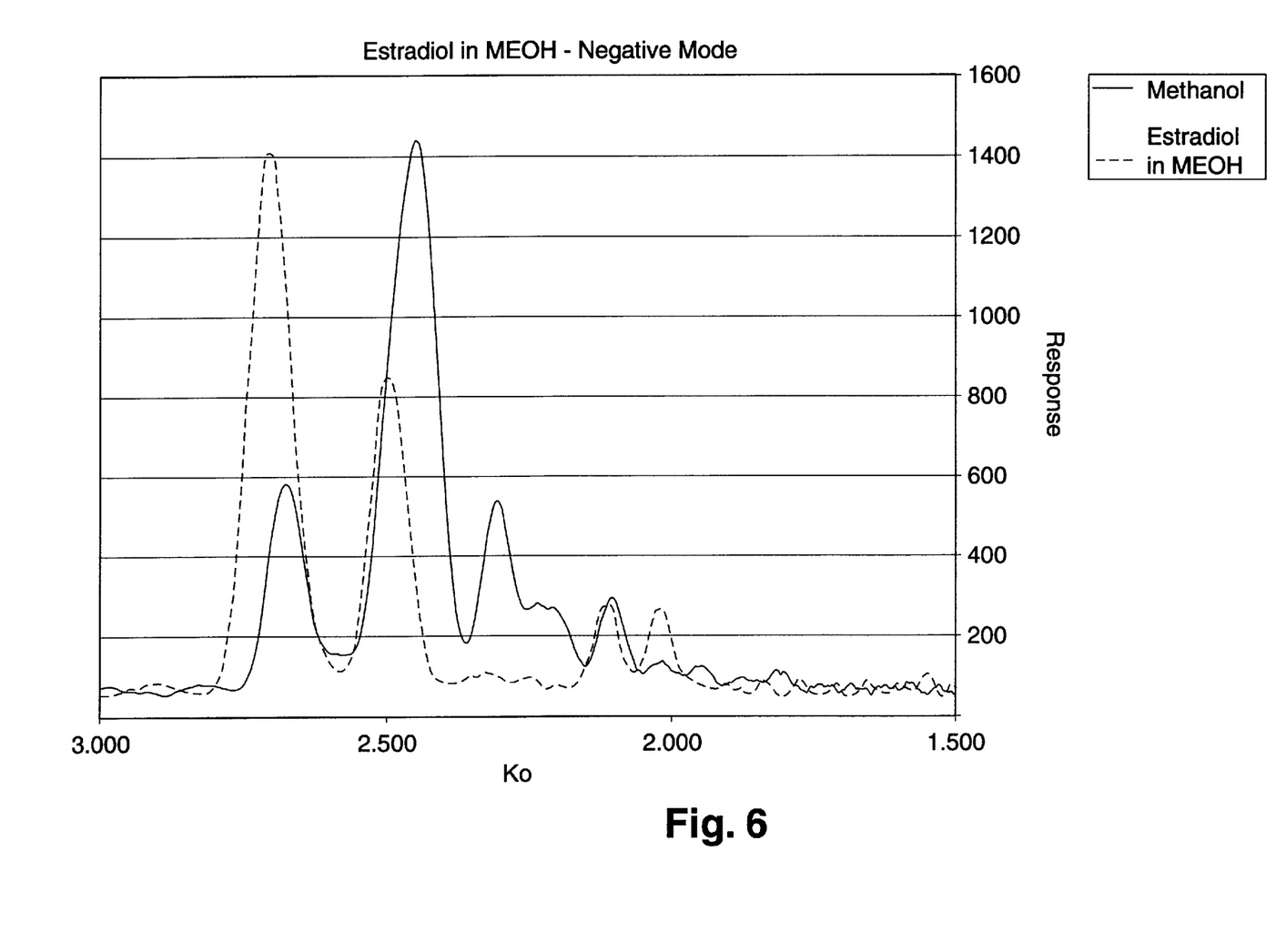
FIG. 6 is a negative mode IMS spectra of estradiol crystals dissolved in methanol.

FIG. 1 is a positive mode IMS spectra of neat estadiol crystals. The peak at a reduced mobility ($K_o$) of 2.8 is the reactant ion peak. Three significant analyte peaks are seen between 2.5 and 1.75. In the negative mode, there were no analyte peaks from neat estradiol crystals (FIG. 2). In acetone solvent, there was no estradiol response in the positive mode (FIG. 3), but there were several peaks in the negative mode (FIG. 4). When the solvent is methanol, there was a shifting of the solvent peaks in positive mode (FIG. 5), and probably only shifting of solvent peaks in negative mode (FIG. 6).

Figure 7:
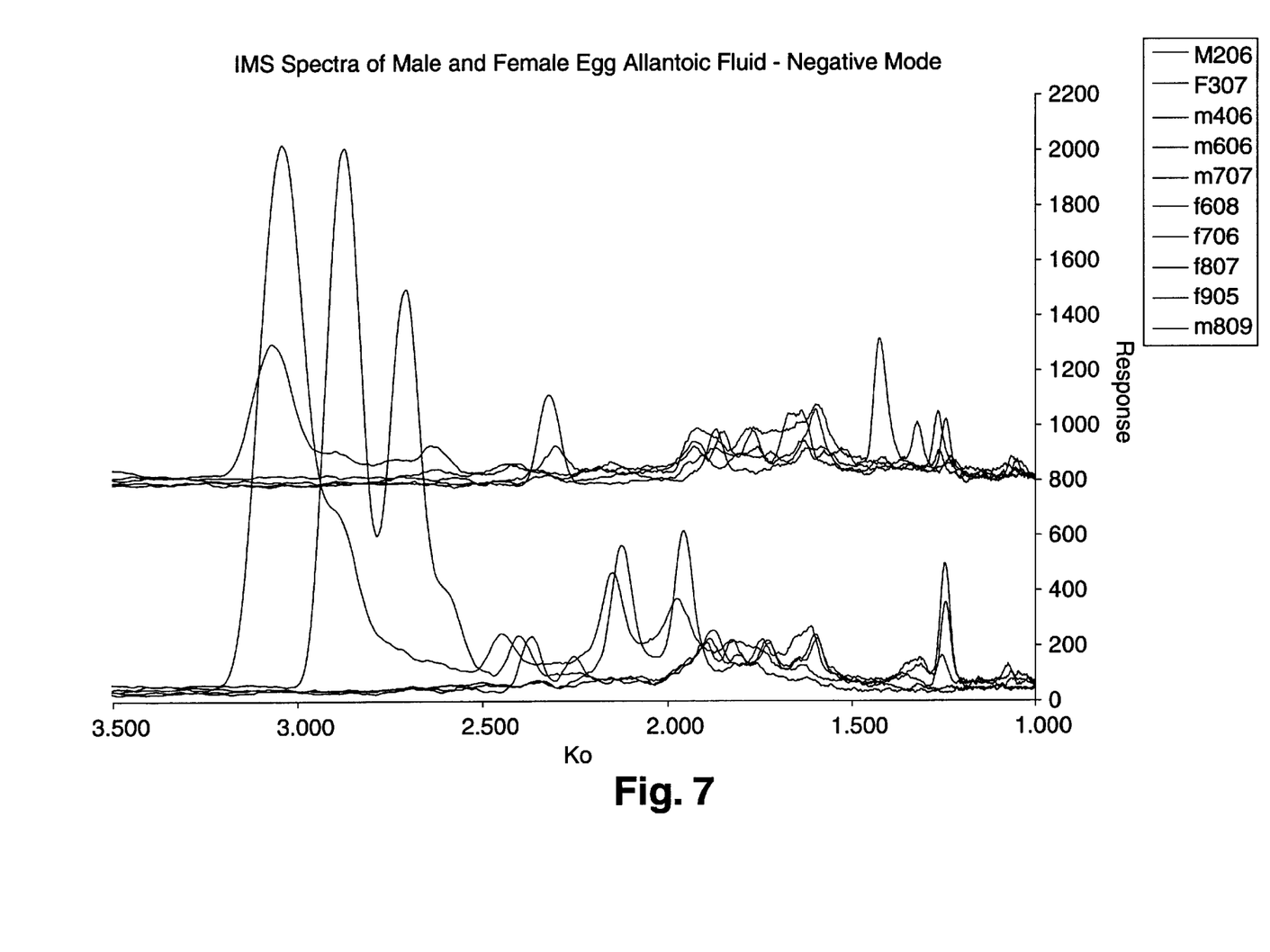
FIG. 7 is a negative mode IMS spectra of 5 (five) male and 5 (five) female allantoic fluid samples.
Figure 8:
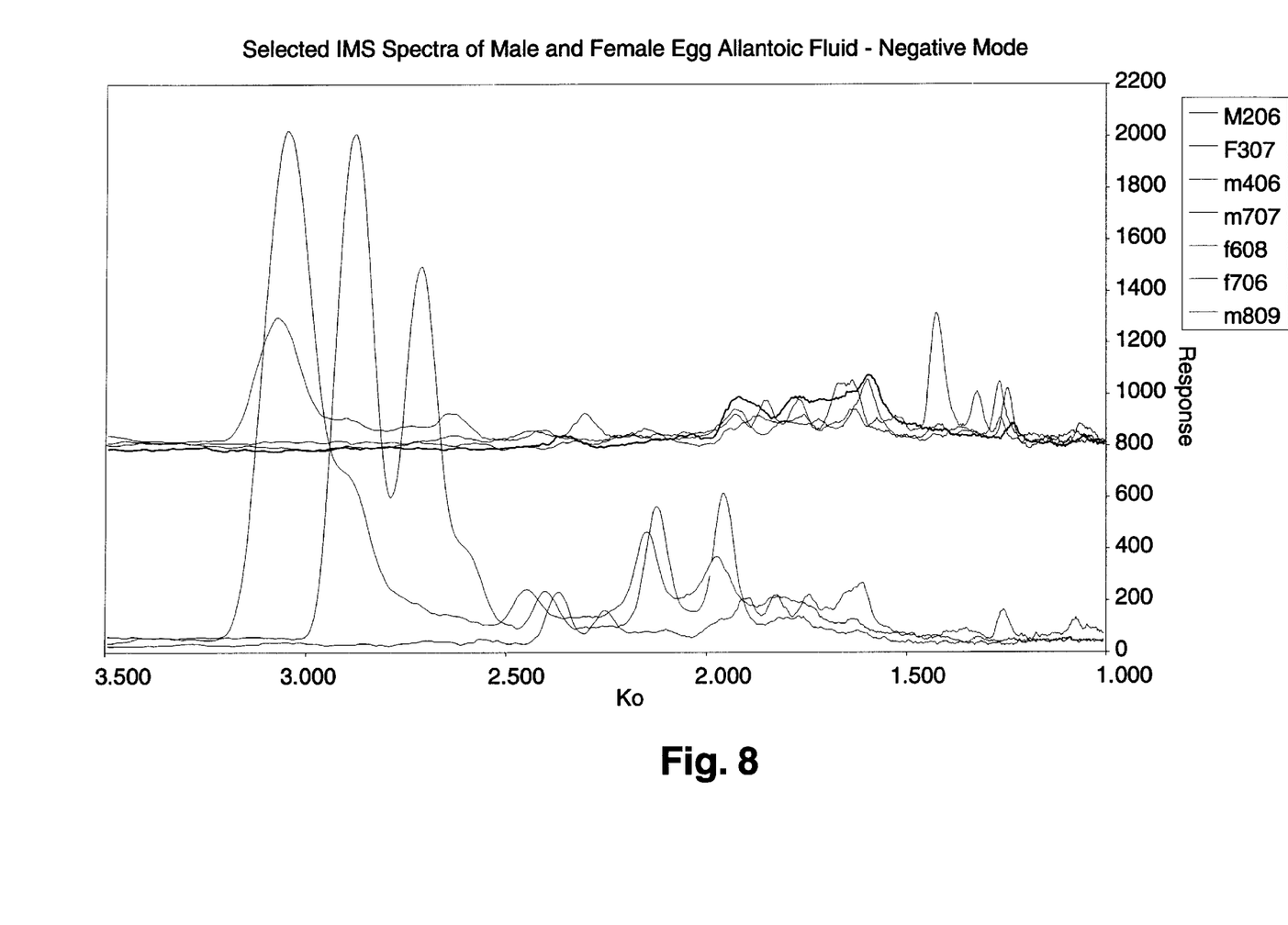
FIG. 8 is a negative mode IMS spectra of 4 (four) male and 3 (three) female allantoic fluid samples selected from FIG. 7.
Figure 9:
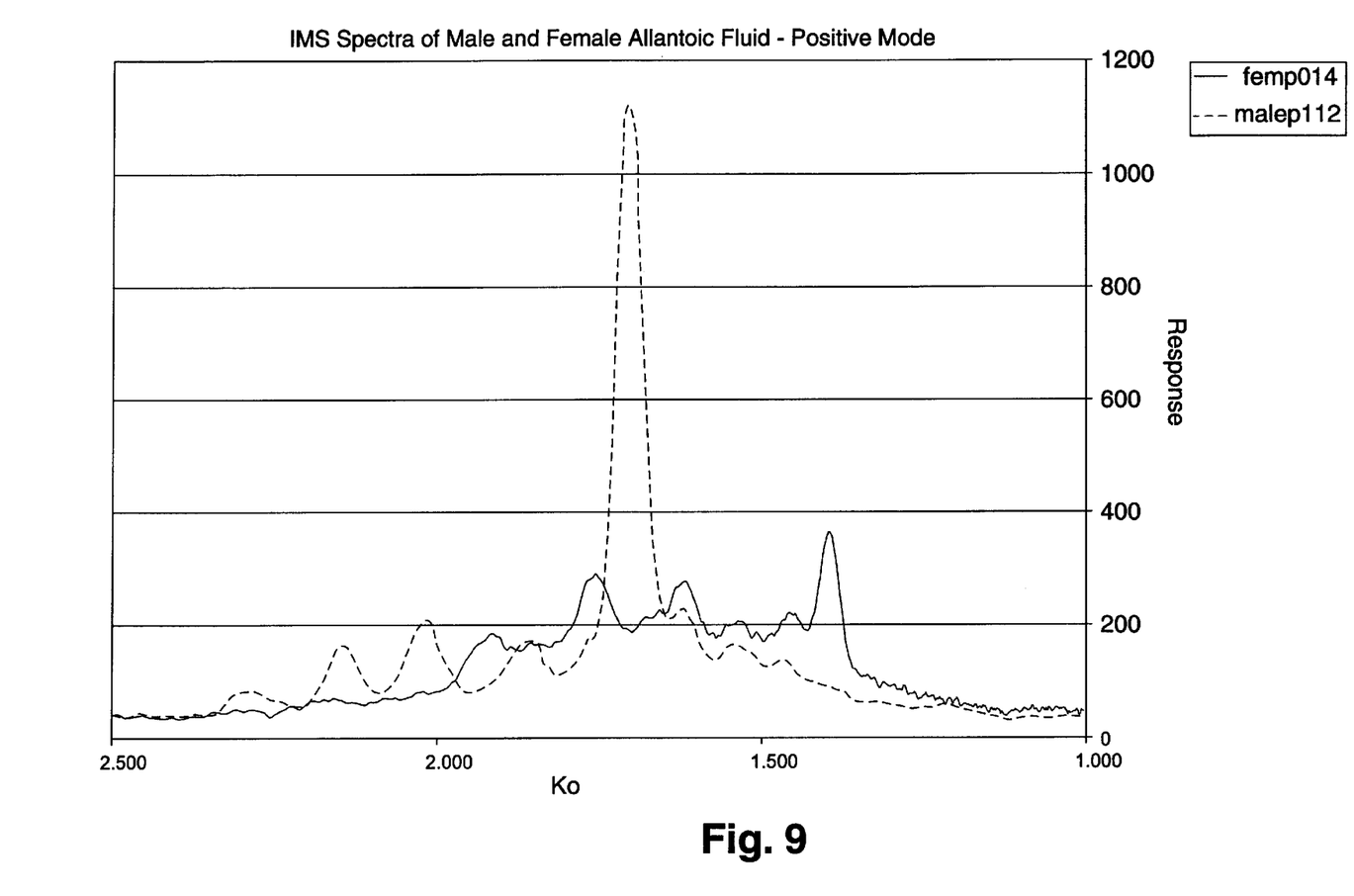
FIG. 9 is a positive mode IMS spectra of 1 (one) male and 1 (one) female allantoic fluid samples.

A total of 10 (ten) male and female allantoic fluid samples were run in negative mode (FIG. 7). In FIG. 7 the males are offset higher than the females for easy comparison. Because of a possible carry-over or instrument memory problem, some of these samples were eliminated in FIG. 8, indicating that there may be significant differences in male and female eggs. The problem may be eliminated in future work by the use of blank solvent injections to verify a clean inlet before each sample run. FIG. 9 has singled out IMS spectra of one female egg and one male egg. Because of clear-out problems with the sample, additional spectra could not be obtained at that time.

Conclusions and Recommendations

Analysis of allantoic fluid in both the positive and negative mode indicates that there may be differences in the chemistry of male and female eggs that are detectable by IMS. Although there is clearly variation in the data derived from the fluids, there are some potentially useful peaks for unique identification. IMS peaks identified in the analysis of neat estradiol and estradiol in solution were generally not recognized in the allantoic fluid samples. The peaks which may provide a unique sex identification have not been chemically identified. Analysis of standards of the additional compounds known to be in allantoic fluid may provide a pathway for peak identification and resolution. Also, IMS/MS analysis may be used to positively identify the peaks of interest, and is currently being considered for future work. Principal component analysis (PCA) is being investigated as a tool to extract sexing data from the spectra which may not be visually obvious.

It should also be noted that the differences were identified in microliter aliquots of fluid, thus providing a potential pathway to integrate the analysis with the industry's current inoculation system. The microliter quantities of allantoic fluid remaining on the inoculation needles may be sampled and analyzed by an automated method, meaning that additional needle sampling into the eggs for sexing would not be necessary, and the sexing and inoculation may take place at the same time with engineered modifications. It should also be noted that the commercial IMS system used in these experiments had clear-down problems with the egg fluids. This was to be expected, given the high complex and involatile nature of biological fluids. It is expected that a successful egg fluid analysis system will require a specially designed IMS tube to maintain high throughput operation over long periods of time.

In summary, the invention comprises IMS analysis of allantoic fluid to provide data which may be used to differentiate male from female eggs and for an integrated sexing and inoculation device to be designed and marketed. An important feature of the preferred method of the invention comprises using extremely small aliquots of fluid, made available because they remain on the inoculation needles used for other procedures, for testing in the IMS system.

Although this invention has been described above with reference to particular means, materials and embodiments, it is to be understood that the invention is not limited to these disclosed particulars, but extends instead to all equivalents within the scope of the following claims.

We claim:

1. A method for gender determination of an avian embryo comprising:

obtaining an allantoic fluid sample from the embryo;

analyzing the sample for a peak of a sex-specific compound in a spectrum from an ion mobility spectrometer; and correlating the sample spectrum peak to differentiate a male from female embryo.

2. The method of claim 1 wherein the sex-specific compound is estradiol.

3. The method of claim 1 wherein the sex-specific compound is dihydrotestosterone.

4. A method for gender determination of an avian embryo comprising:

obtaining an allantoic fluid sample from the embryo by a method comprising inserting a needle through an egg shell into the egg, removing the needle, and removing allantoic fluid from the needle for use as said sample;

analyzing the sample for a peak of a sex-specific compound in a spectrum from an ion mobility spectrometer; and correlating the sample spectrum peak to differentiate a male from female embryo.

5. The method of claim 4, wherein said sample is obtained from the needle used for inoculation of the egg.

6. The method of claim 4 wherein the sex-specific compound is estradiol.

7. The method of claim 4 wherein the sex-specific compound is dihydrotestosterone.

* * * * *